(12) United States Patent
Siljamäki et al.

(10) Patent No.: US 10,143,856 B2
(45) Date of Patent: Dec. 4, 2018

(54) METHOD AND APPARATUS PERTAINING TO TREATING A PATIENT USING HEAVY PARTICLES

(71) Applicant: Varian Medical Systems International AG, Cham (CH)

(72) Inventors: Sami P. Siljamäki, Helsinki (FI); Janne I. Nord, Espoo (FI)

(73) Assignee: Varian Medical Systems International AG, Steinhausen (CH)

( * ) Notice: Subject to any disclaimer, the term of this patent is extended or adjusted under 35 U.S.C. 154(b) by 111 days.

(21) Appl. No.: 15/086,417

(22) Filed: Mar. 31, 2016

(65) Prior Publication Data

US 2017/0281974 A1    Oct. 5, 2017

(51) Int. Cl.
*A61N 5/10* (2006.01)

(52) U.S. Cl.
CPC ......... *A61N 5/1048* (2013.01); *A61N 5/1043* (2013.01); *A61N 5/1045* (2013.01); *A61N 5/1081* (2013.01); *A61N 2005/1074* (2013.01); *A61N 2005/1087* (2013.01)

(58) Field of Classification Search
CPC ................ A61N 5/1048; A61N 5/1081; A61N 2005/1074; A61N 2005/1087

USPC ................ 250/396 R, 492.1, 492.3
See application file for complete search history.

(56) References Cited

U.S. PATENT DOCUMENTS

| | | | |
|---|---|---|---|
| 2012/0108958 A1* | 5/2012 | Jackson | A61N 5/10 600/427 |
| 2013/0066135 A1* | 3/2013 | Rosa | A61N 5/10 600/1 |
| 2015/0343238 A1* | 12/2015 | Balakin | A61N 5/1069 600/1 |

* cited by examiner

*Primary Examiner* — Nicole Ippolito
(74) *Attorney, Agent, or Firm* — Fitch, Even, Tabin & Flannery LLP

(57) ABSTRACT

A heavy-particle treatment system exposes a patient's treatment volume, during the course of a single treatment session, to beams of heavy particles from a variety of different angles. The source of heavy particles may rotate about the patient to facilitate that variety of different angles. The foregoing can occur pursuant to a treatment plan that accounts for a penetration range as corresponds to the beams of heavy particles and for using at least one lateral beam controlling device to control at least one of the beams of heavy particles.

17 Claims, 3 Drawing Sheets

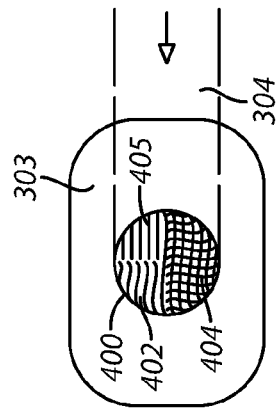
FIG. 4.1
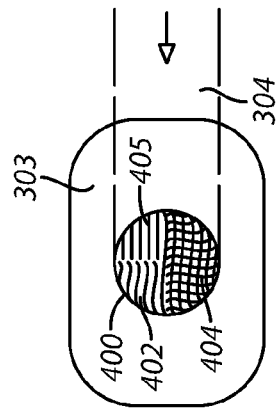
FIG. 4.2
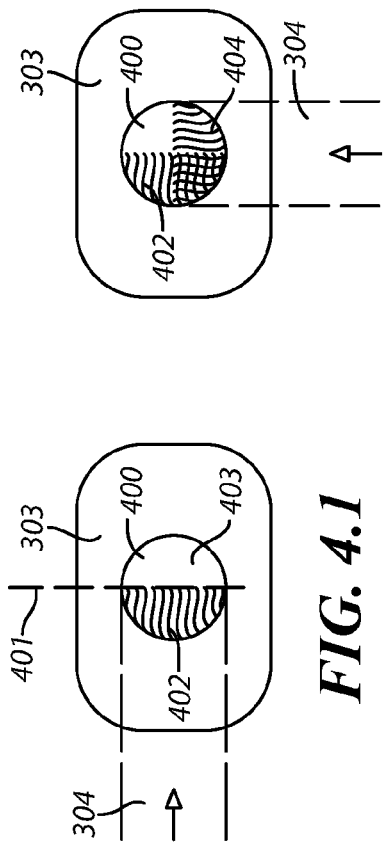
FIG. 4.3
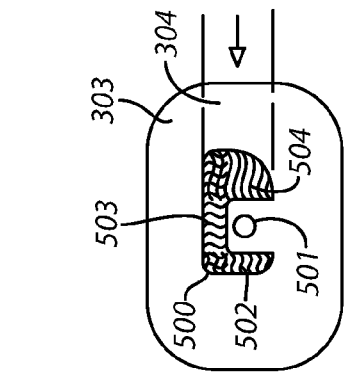
FIG. 5.1
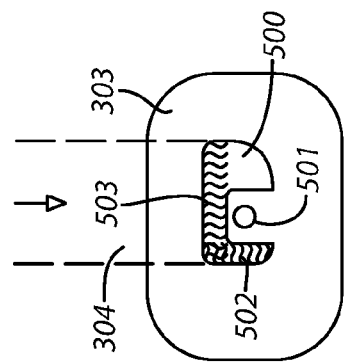
FIG. 5.2
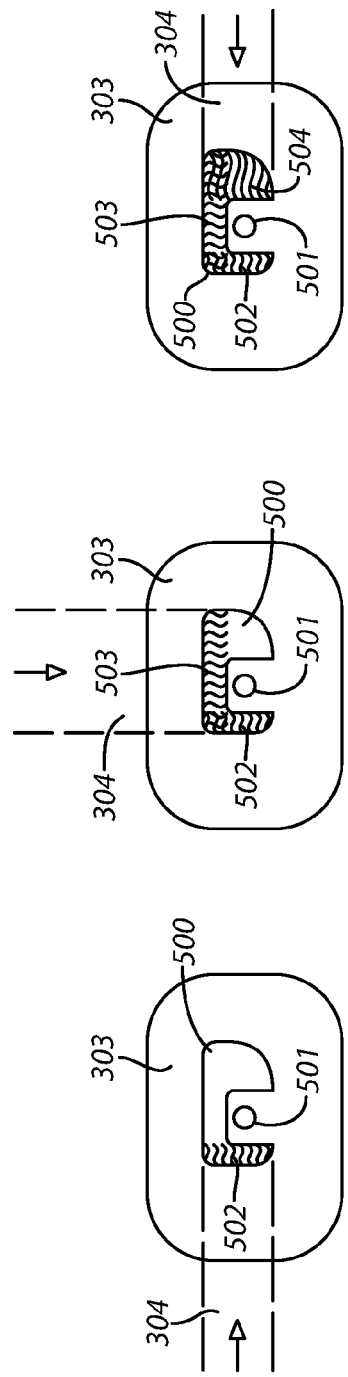
FIG. 5.3

METHOD AND APPARATUS PERTAINING TO TREATING A PATIENT USING HEAVY PARTICLES

TECHNICAL FIELD

This invention relates generally to the use of heavy particles to treat a patient.

BACKGROUND

Radiation therapy is known in the art. Generally speaking, such therapy typically involves exposing an unwanted volume on or within a patient's body to high-energy photonic radiation (such as, but not limited to, x-rays). This radiation often serves to destroy the irradiated cellular material and hence reduce or eliminate the unwanted volume. In many cases such radiation is periodically administered over time (days, weeks, or months) in a series of discrete treatment sessions.

Many treatment plans provide for exposing the patient's target volume to such radiation from a number of different directions. Arc therapy, for example, comprises one such approach. In such a case it often becomes necessary to adjust the delivery of the radiation during such a treatment in order to avoid collateral harm and/or to best ensure the desired dosage distribution.

Heavy particles are sometimes also used for a similar purpose, albeit often in a dissimilar way. Heavy particles (such as protons, heavy ions, antiprotons, and pions) behave considerably different than the photons of more traditional radiation sources such as x-rays. As a result, it is not possible to simply exchange a heavy-particle source for a photonic radiation source in many treatment systems (such as, for example, an arc therapy system) as the desired results of such treatment will not be inherently met. Instead, an inadequate (or otherwise inappropriate) dosage of the treatment volume and/or undesired (and avoidable) harm to other portions of the patient's body can result.

BRIEF DESCRIPTION OF THE DRAWINGS

The above needs are at least partially met through provision of the method and apparatus pertaining to treating a patient using heavy particles described in the following detailed description, particularly when studied in conjunction with the drawings, wherein:

FIGS. 4.1-4.3 comprise top-plan schematic views as configured in accordance with various embodiments of the invention; and FIGS. 5.1-5.3 comprise top-plan schematic views as configured in accordance with various embodiments of the invention.

Figure 1:
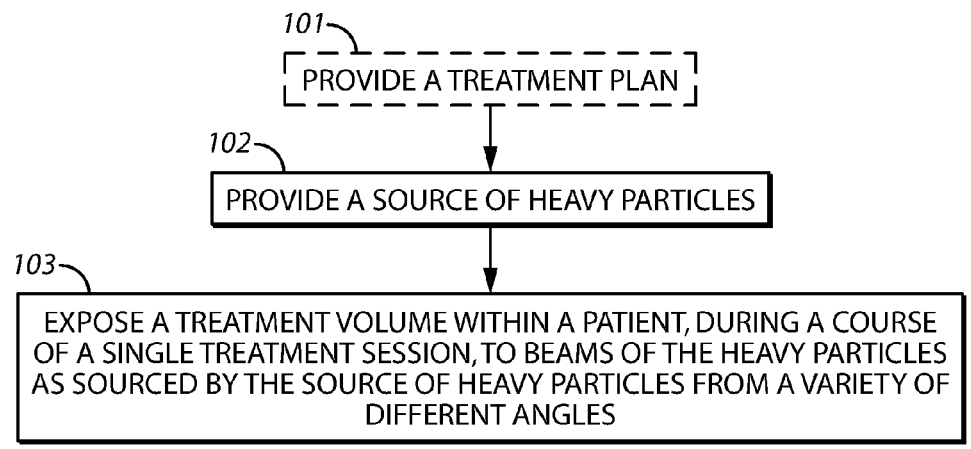
FIG. 1 comprises a flow diagram as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments provide for exposing a patient's treatment volume, during the course of a single treatment session, to beams of heavy particles as sourced by a source of heavy particles from a variety of different angles. These heavy particles may consist, for example, of one or more of protons, heavy ions, antiprotons, and pions. By one approach, the source of heavy particles rotates about the patient to facilitate that variety of different angles.

By one approach the foregoing occurs pursuant to a treatment plan. This treatment plan can account, by one approach, for a penetration range as corresponds to the beams of heavy particles. This consideration of the penetration range can include, at least in part, accounting for the corresponding anticipated spread-out Bragg peak characteristic.

Such a treatment plan can further provide for using at least one lateral beam controlling device to control at least one of the beams of heavy particles. Such a lateral beam controlling device can comprise, for example, one or more steering magnets and/or one or more multi-leaf collimators. In lieu of the foregoing or in combination therewith, the treatment plan can also provide for using at least one dynamic proton range adjuster to control a penetration range of at least one of the beams of heavy particles. Such a dynamic proton range adjuster can comprise, for example, one or more of an energy selector (for the heavy-particle source), a dynamically adjustable material thickness, and a range modulator wheel.

So configured, these teachings can provide, for example, for rotating a source of heavy particles about a patient and selectively varying an overall intensity level of the heavy particles as a function of a corresponding angle of the heavy-particle source with respect to the treatment volume. The latter can comprise, for example, using a lateral beam controller to laterally confine the beams as a function of the corresponding angle and/or adjusting a heavy-particle range as a function of the corresponding angle.

These teachings permit and facilitate the appropriate leveraging of certain characteristics of heavy-particle beams for therapeutic purposes in an application setting that heretofore has been largely relegated to photonic delivery systems. The concepts and details set forth herein are readily scalable and highly flexible in practice and will readily accommodate, for example, making at least some changes during the treatment session to the overall intensity level of the heavy particles within, say, a sub-millisecond time scale.

Figure 2:
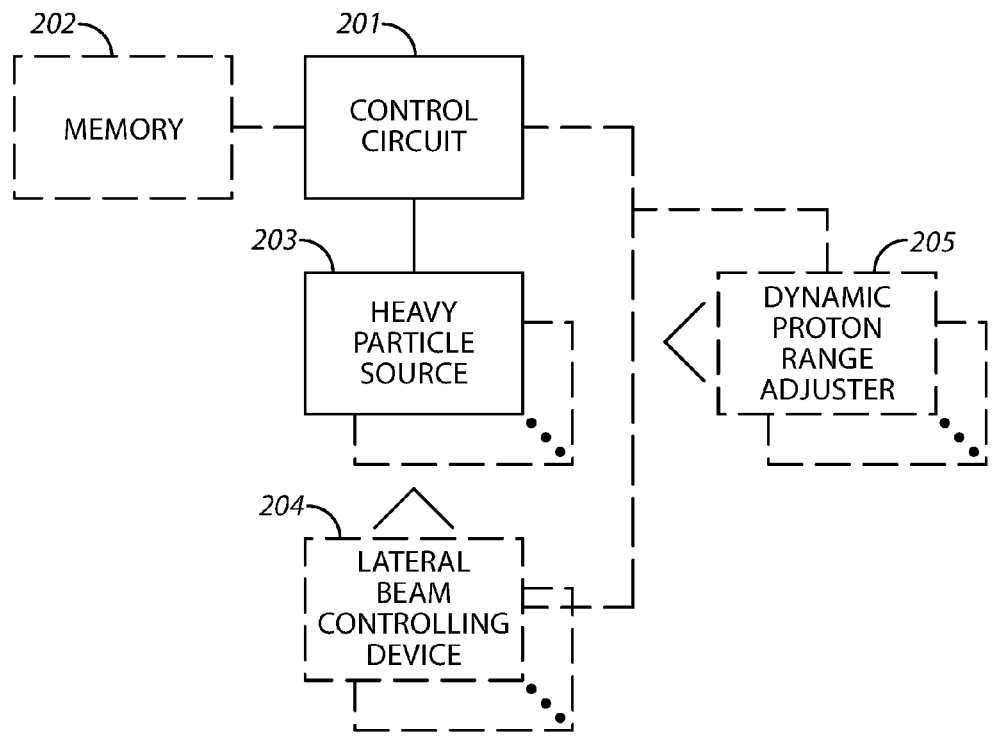
FIG. 2 comprises a block diagram as configured in accordance with various embodiments of the invention.

These and other benefits may become clearer upon making a thorough review and study of the following detailed description. Referring now to the drawings, and in particular to FIGS. 1 and 2, an illustrative process 100 and corresponding treatment platform 200 that are compatible with many of these teachings will be presented.

If desired, this process 100 can optionally include the step 101 of providing a treatment plan. A treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represents a worthy compromise between the desired therapeutic result and the avoidance of undesired collateral effects.

The treatment platform 200 includes a control circuit 201. Such a control circuit 201 can comprise a fixed-purpose hard-wired platform or can comprise a partially or wholly programmable platform. These architectural options are well known and understood in the art and require no further description here. This control circuit 201 is configured (for example, by using corresponding programming as will be well understood by those skilled in the art) to carry out one or more of the steps, actions, and/or functions described herein including but not limited to the aforementioned treatment plan.

By one optional approach the treatment platform 200 includes a memory 202 that may be integral to the control circuit 201 or that can be physically discrete (in whole or in part) from the control circuit 201 as desired. This memory 202 can also be local with respect to the control circuit 201 (where, for example, both share a common circuit board, chassis, power supply, and/or housing) or can be partially or wholly remote with respect to the control circuit 201 (where, for example, the memory 202 is physically located in another facility, metropolitan area, or even country as compared to the control circuit 201).

This memory 202 can serve, for example, to non-transitorily store the computer instructions, including the aforementioned treatment plan, that, when executed by the control circuit 201, cause the control circuit 201 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

At step 102 this process 100 provides a source 203 of heavy particles. As used herein this reference to "heavy particles" will be understood to refer to one or more of protons, heavy ions, antiprotons, and pions. It will be further understood that this reference to "heavy particles" generally excludes photons of varying energy levels (though the present teachings regarding the use of heavy particles may be combined with photonic practices if desired in an appropriate application setting).

Figure 3:
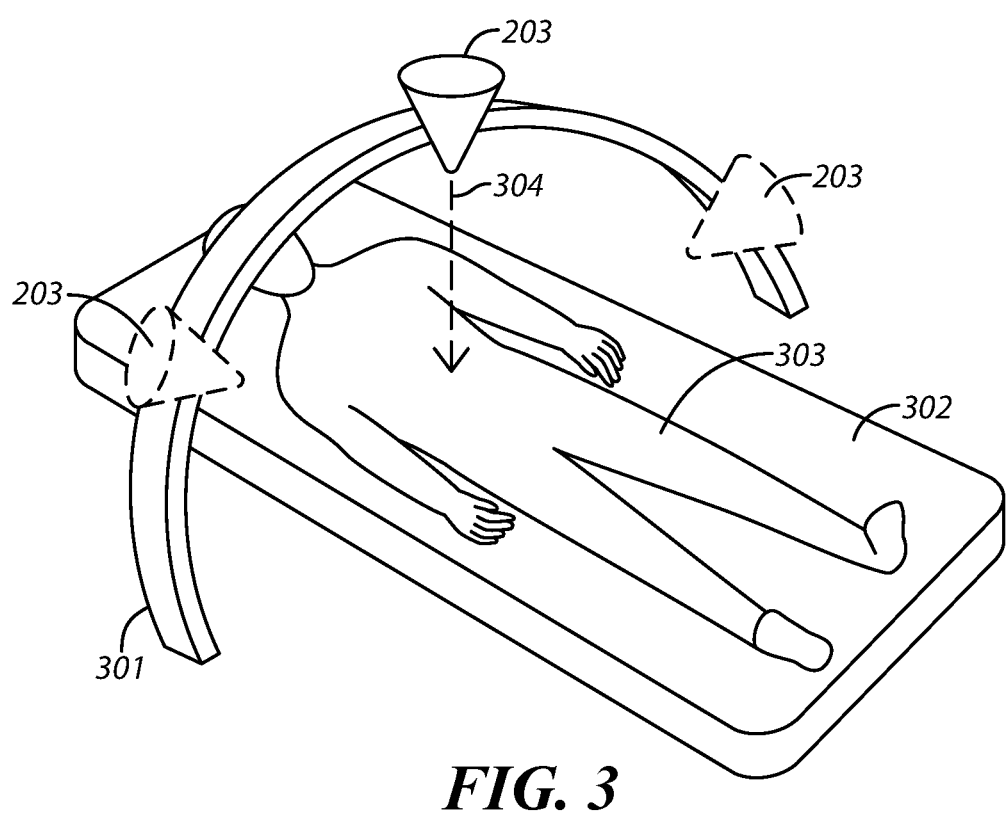
FIG. 3 comprises a perspective schematic view as configured in accordance with various embodiments of the invention.

Referring momentarily to FIG. 3, this heavy-particle source 203 can be configured to move with respect to a patient 303 who rests, for example, atop a patient-support surface 302. More particularly, this movement can occur during the course of a single treatment session for the patient. In this particular illustrative example the heavy-particle source 203 is mounted to a gantry 301 that circumscribes a half-circle about the patient 303. If desired, of course, the gantry 301 can comprise a lesser arc or an arc of greater magnitude (up to and including a full circle that fully circumscribes the patient 303). So configured, the heavy-particle source 203 can move (continuously or intermittently as desired) about the patient 303 during a given treatment session to thereby direct a heavy-particle beam 304 towards a treatment volume within the patient 303 from a variety of treatment angles.

While there is a superficial similarity between the appearance of such an approach and that of, say, arc therapy using photonically-based x-rays, unfortunately the aforementioned treatment plan cannot be formed by simply repurposing existing arc therapy treatment planning algorithms. To put this simply, one can think of a therapeutically-useful arc therapy-based delivery of high-energy photons as comprising a two-dimensional problem space (more or less akin to framing a field of view when taking a picture with an ordinary camera). This is because many of the photons in such a process, to some large extent, are expected to pass completely through the treatment volume and the patient, hence rendering the third dimension of depth an essentially uncontrollable vector.

Photons have very soft distal penumbra. To some reasonable extent one could even say that there is no effective penumbra within the treatment setting as the dose only decays slowly as the beam propagates deeper and deeper into the patient. It is this very effect that enables photon-based arc therapy. In the absence of steep penetration gradients, it is possible to modulate the photon beam in only two dimensions along the arc (using, for example, a multileaf collimator) and obtain a rather uniform dose distribution for the target.

Heavy particles such as protons, however, behave quite differently from photons in these regards. In particular, to some considerable extent most of the heavy particles will in fact stop before exiting the patient's body. The greatest depth of penetration for a given heavy-particle beam is typically represented by its anticipated Spread-Out Bragg Peak (SOBP) characteristic. Accordingly, a treatment plan to effectively utilize heavy particles as the therapeutic vector as per these teachings will typically take into account the penetration range as corresponds to the beam of heavy particles as represented, for example, by the SOBP characteristic for such a beam.

FIGS. 4.1 through 4.3 provide one illustrative example in these regards. In this example a beam 304 of heavy particles is directed at a treatment target 400 within a patient 303. With initial reference to FIG. 4.1, these heavy particles have a maximum depth of penetration represented by the phantom line denoted by reference numeral 401. Thus, only a first portion 402 of the treatment target 400 receives a dosage from this particular treatment angle.

The angle of the beam 304 is shifted 90 degrees in FIG. 4.2. This treatment angle results in a corresponding dosage area 404 that partially overlaps with the first portion 402 noted above. In FIG. 4.3 the beam 304 has shifted another 90 degrees to yield another dosage area 405 that partially overlaps with the second dosage area 404 noted above.

It can be seen from the foregoing example that a given treatment volume can be successfully dosed with heavy particles. The dosage distribution, however, is owing to due consideration for not only the beam aperture/shape but also for the depth-of-penetration of each particular beam.

FIGS. 5.1 through 5.3 provide another illustrative example in these regards. In this example the treatment volume 500 is irregularly shaped. In addition, this treatment volume 500 partially envelopes another critical patient structure 501 that must, to the extent possible, be avoided during dosing. By properly controlling both the beam's 304 two-dimensional lateral shape as well as its depth-of-penetration characteristics at the three different illustrated treatment angles, various portions 502, 503, and 504 of the treatment volume 500 can be successfully dosed with heavy particles while simultaneously avoiding the critical structure 501 notwithstanding that the latter is directly coaxial with the beam 304 in each illustrated treatment field.

Again, however, such results cannot be expected by simply employing existing two-dimensional thinking in conjunction with, for example, arc therapy photon-delivery treatment platforms. If one were to modulate the delivery of heavy particles such as protons in only two lateral dimensions using, say, a multi-leaf collimator, the result would likely comprise a very noisy dose distribution inside the treatment target that included numerous undue hot spots, cold spots, and so forth.

We have also determined that the delivery of heavy particles is dependent upon the treatment-platform hardware (both in lateral and longitudinal directions) to a degree that does not apply to the delivery of photons. These control mechanisms may in fact all operate on different time scales (minutes vs. second vs. milliseconds vs. microseconds) in order to avoid unwanted interference. With a rotational treatment, an additional time scale is added: the gantry rotation timescale (typically measured in the passage of minutes). Time considerations in these regards are, of course, typically non-applicable when treating a patient with a photon-based dosing.

As a result, many of the dosage-forming tools common to photon-based arc therapy treatments are not combinable in similar ways to support the useful administration of a dosage of heavy particles.

With the foregoing in mind, and referring again to FIG. 2 the illustrated treatment-administration system 200 can optionally include one or more lateral beam controlling devices 204 and/or one or more dynamic proton range adjusters 205.

The lateral beam controlling device(s) 204 can comprise, for example, one or more multi-leaf collimators or steering magnets that are controlled, from moment to moment, by the control circuit 201. This can comprise, for example, controlling the shape of the multi-leaf collimator's aperture and/or relative position with respect to the heavy-particle source's 203 beam 304 or controlling the relative strength and orientation/location of one or more steering magnets and in turn influencing the shape and/or direction of the beam 304.

The dynamic proton range adjuster(s) 205 can comprise, for example, one or more energy selectors (i.e., the energy of the beam 304 at a given moment in time and/or at a given gantry position/angle), dynamically adjustable material thicknesses (such as a plurality of plates of a given material (or variety of materials) than can be selectively placed in the beam's path), or range modulator wheels as are known in the art. As with the lateral beam controlling devices 204, these dynamic proton range adjusters 205 can also be operably coupled to the control circuit 201 to permit the latter to control, from moment to moment, the former in order to thereby dynamically control a maximum penetration depth of the heavy-particle beam 304 at different moments (and at different angles) of the treatment session.

So configured, the control circuit 201 can implement a treatment plan that provides for three spatial dimensions of control as regards delivery of a beam 304 of heavy particles to a given treatment target from a variety of different angles. In addition, these teachings will readily accommodate making changes to the settings of the treatment system 200 during a given treatment session to, for example, the overall intensity level of the heavy particles within a sub-millisecond time scale if desired. In fact, many of the aforementioned beam-control mechanisms are operable within a similarly small time frame. For example, a magnetically-controlled beam can be redirected in a sub-millisecond time scale to effectively produce a wide field with varying two-dimensional intensity for each gantry angle. As another example, a range modulator wheel operating as a beam range-adjustment device can also function within only a few milliseconds. This temporal flexibility is again quite unlike the ordinary circumstances that attend the delivery of a photon-based beam for therapeutic purposes.

Referring again to FIGS. 1 and 2, at step 103 this process 100 provides for exposing a treatment volume within a patient, during the course of a single treatment session (as versus a number of discrete treatment sessions that are separated by time over many hours, days, weeks, or the like), to beams of heavy particles as sourced by a source of heavy particles from a variety of different angles. As noted above, this step 103 can comprise, at least in part, executing a corresponding treatment plan in these regards. As an illustrative example in these regards, this treatment plan can comprise, at least in part, selectively varying an overall intensity level of the heavy particles as a function of a corresponding angle as regards the source 203 and the treatment volume and during the course of rotating the heavy-particle source 203 about the patient. This selective variation of the overall intensity level of the heavy particles can comprise using a lateral beam controller 204 to laterally confine the beams as a function of the corresponding angle and/or adjusting a heavy-particle range via a dynamic proton range adjuster 205 as a function of the corresponding angle.

As note above, such a treatment plan can be generated, if desired, via a corresponding optimization process. By one approach, for example, such a process can provide for automatically generating an initial guess for various ones of the degrees of freedom for various aspects of the treatment-delivery platform 200. The optimization process can then increment and/or decrement various ones of those degrees of freedom to attempt to improve the estimated therapeutic result. The clinical objectives can be defined by the user and can include, for example, traditional dose-volume constraints or other objectives as may be desired.

For example, the initially-generated treatment machine parameters can include starting and stopping ranges (the SOBP length) for each angle/field. These parameters can be calculated directly from the know/observed target/patient geometry in many instances. The available dynamic range adjuster can be used, for example, to produce an SOBP for each available beam direction. For the perpendicular direction (i.e., perpendicular to the beam's axis of travel), the initial optimization guess can conform to the target outline while also excluding user-defined critical organs. The beam's perpendicular shape can be created, for example, using a dynamic multi-leaf collimator that acts as a lateral beam controlling device.

The optimization method can then calculate optimal configurations of all the available control devices over (possibly, a plurality of) gantry rotations to thereby fullfill clinical objectives to the largest possible extent. In this example, the optimization method adjusts the multi-leaf collimator leaf positions, beam starting and stopping ranges, and overall beam intensity as a function of the gantry angle.

As another illustrative example in these regards, the heavy-particle beam is controlled using fast magnetic steering (the magnets serving as the aforementioned lateral beam controlling device 204) and fast intensity variation to effectively produce a modulated two-dimensional intensity for each beam direction. By one approach, the range variation speed is slow (on par with, for example, the speed of the gantry's movement) and as a result only a single range ("zero-width SOBP") is given from each beam direction. In this case, numerous dynamic proton range adjustment devices will serve suitably. By another approach, the SOBP has finite (and variable) width from each direction. In this case a quick proton range adjustment device, such as a fast range modulator wheel, will serve well.

Presuming the foregoing, the treatment-plan optimization approach can use constant initial guesses for the two-dimensional beam intensity distributions (though still presuming that the beam conform to the target minus critical structures), and the SOBP starting and stopping ranges can be defined based again on the target geometry. The two-dimensional intensity distribution can then be optimized for each gantry angle.

Using the approaches set forth herein one or more sources of heavy particles can be successfully employed to deliver a therapeutic dose to a patient's treatment volume from a variety of different angles. This greatly improves upon the typical use of heavy particles in these regards and provides a treatment capability that offers some characterizing attributes that are highly unlike those of photon-delivery systems and hence potentially more useful for at least some patients.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method comprising:
providing a source of heavy particles that comprise at least one of antiprotons and pions, wherein the source of heavy particles is movably mounted to a gantry that forms an arcuately-shaped pathway about a patient such that the source of heavy particles can be selectively rotated about at least a part of the patient;
exposing a treatment volume within the patient, during a course of a single treatment session, to beams of the heavy particles as sourced by the source of heavy particles from a variety of different angles as the source of heavy particles rotates about at least a part of the patient.

2. The method of claim 1 further comprising:
providing a treatment plan;
wherein exposing the treatment volume to beams of the heavy particles comprises using the treatment plan to govern exposing the treatment volume to the beams of the heavy particles.

3. The method of claim 2 wherein the treatment plan comprises, at least in part, accounting for a penetration range as corresponds to the beams of the heavy particles.

4. The method of claim 3 wherein accounting for a penetration range as corresponds to the beams of the heavy particles comprises, at least in part, accounting for a corresponding anticipated spread-out Bragg peak (SOBP) characteristic.

5. The method of claim 2 wherein the treatment plan provides for using at least one lateral beam controlling device to control at least one of the beams of heavy particles.

6. The method of claim 5 wherein the at least one lateral beam controlling device comprises at least one of:
at least one steering magnet; and
at least one multi-leaf collimator.

7. The method of claim 2 wherein the treatment plan provides for using at least one dynamic proton range adjuster to control a penetration range of at least one of the beams of heavy particles.

8. The method of claim 7 wherein the dynamic proton range adjuster comprises at least one of:
an energy selector;
a dynamically adjustable material thickness;
a range modulator wheel.

9. The method of claim 2 wherein the treatment plan comprises, at least in part:
while rotating the source of heavy particles about the patient, selectively varying an overall intensity level of the heavy particles as a function of a corresponding angle by at least one of:
using a lateral beam controller to laterally confine the beams as a function of the corresponding angle; and
adjusting a heavy-particle range as a function of the corresponding angle.

10. The method of claim 9 wherein the treatment plan provides for making at least some changes during the treatment session to the overall intensity level of the heavy particles within a sub-millisecond time scale.

11. An apparatus comprising:
a source of heavy particles that comprise at least one of antiprotons and pions, wherein the source of heavy particles is movably mounted to a gantry that forms an arcuately-shaped pathway about a patient such that the source of heavy particles can be selectively rotated about at least a part of the patient;
a control circuit operably coupled to the source of heavy particles and configured to expose a treatment volume within the patient, during a course of a single treatment session, to beams of the heavy particles as sourced by the source of heavy particles from a variety of different angles as the source of heavy particles rotates about at least a part of the patient.

12. The apparatus of claim 11 wherein in the control circuit is configured to use a treatment plan to govern exposing the treatment volume to the beams of the heavy particles.

13. The apparatus of claim 12 wherein the treatment plan comprises, at least in part, accounting for a penetration range as corresponds to the beams of the heavy particles.

14. The apparatus of claim 12 wherein the treatment plan provides for using at least one lateral beam controlling device to control at least one of the beams of heavy particles.

15. The apparatus of claim 14 wherein the at least one lateral beam controlling device comprises at least one multi-leaf collimator.

16. The apparatus of claim 12 wherein the treatment plan provides for using at least one dynamic proton range adjuster to control a penetration range of at least one of the beams of heavy particles.

17. The apparatus of claim 16 wherein the dynamic proton range adjuster comprises at least one of:
an energy selector;
a dynamically adjustable material thickness;
a range modulator wheel.

* * * * *